(12) United States Patent
Mollus et al.

(10) Patent No.: US 7,340,033 B2
(45) Date of Patent: Mar. 4, 2008

(54) X-RAY UNIT HAVING AN AUTOMATICALLY ADJUSTABLE COLLIMATOR

(75) Inventors: Sabine Mollus, Aachen (DE); Jürgen Weese, Aachen (DE); Henning Braess, Lutherville (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 106 days.

(21) Appl. No.: 10/566,665

(22) PCT Filed: Jul. 19, 2004

(86) PCT No.: PCT/IB2004/051249

§ 371 (c)(1),
(2), (4) Date: Jan. 27, 2006

(87) PCT Pub. No.: WO2005/009243

PCT Pub. Date: Feb. 3, 2005

(65) Prior Publication Data

US 2006/0203966 A1    Sep. 14, 2006

(30) Foreign Application Priority Data

Jul. 30, 2003   (EP)   .................................. 03102349

(51) Int. Cl.
  *G01N 23/04* (2006.01)
(52) U.S. Cl. ........................................ 378/62; 378/147
(58) Field of Classification Search ........ 378/147–153, 378/62, 98.2, 98, 116, 145, 156, 159, 108
See application file for complete search history.

(56) References Cited

U.S. PATENT DOCUMENTS

| 4,609,940 | A |   | 9/1986  | Born et al. |
| 4,875,225 | A |   | 10/1989 | Hunold |
| 5,287,396 | A | * | 2/1994  | Stegehuis ................ 378/98.2 |
| 5,369,678 | A | * | 11/1994 | Chiu et al. ................. 378/62 |
| 5,394,455 | A | * | 2/1995  | Roeck et al. ............. 378/98.3 |
| 6,055,259 | A |   | 4/2000  | Frey et al. |
| 6,055,295 | A |   | 4/2000  | Murthy et al. |
| 6,215,853 | B1 | * | 4/2001  | Kump et al. .............. 378/151 |
| 6,501,828 | B1 | * | 12/2002 | Popescu .................... 378/150 |

FOREIGN PATENT DOCUMENTS

| DE | 3030332 A1 | 2/1982 |
| EP | 1065670 A2 | 1/2001 |

OTHER PUBLICATIONS

T.M. Buzug, J. Weese: "Image registration for DSA quality enhancement", Comput. Med. Imag. Graph. 1998, 22, 103.

(Continued)

*Primary Examiner*—Hoon Song

(57) ABSTRACT

The invention relates to a method and a unit for automatically adjusting a collimator (6). In this connection, a region (9) of interest inside the body is determined in an application-specific way from an analysis of first X-ray pictures, and the collimator (6) is then adjusted thereon. The region (9) of interest can, in particular, be chosen to be large enough for the irradiation field to cover all those positions of an organ (10) of interest that occur as a result of heartbeat and/or respiration. Preferably, a movement estimate' is undertaken during a current examination in order to be able to readjust the collimator (6) if necessary. If the region of interest cannot be localized, the collimator (6) is opened to a standard adjustment.

10 Claims, 1 Drawing Sheet

OTHER PUBLICATIONS

Figure 1:
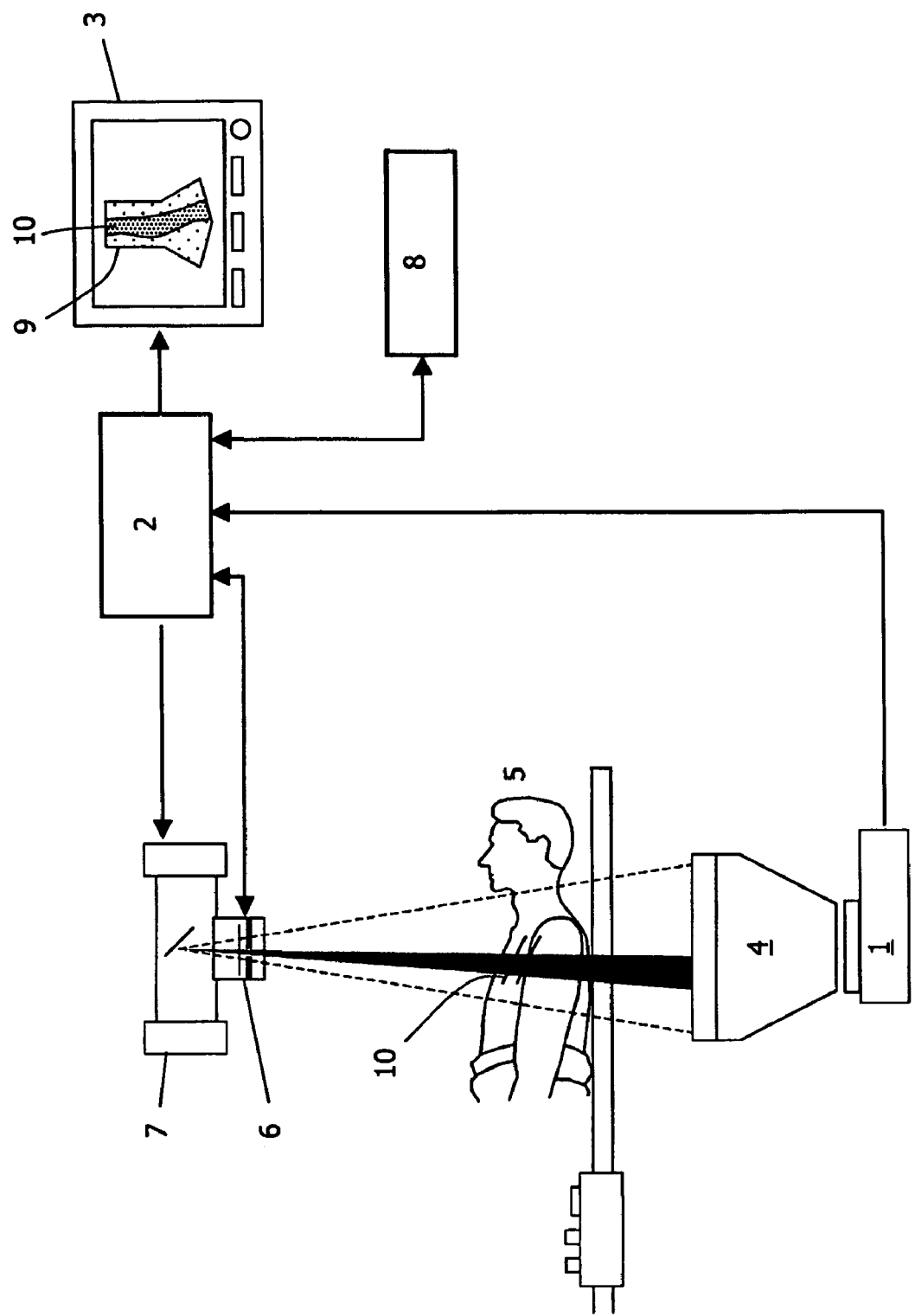

T.M. Buzug, J. Weese: "Voxel-based similiarity measures for medical image registration in radiological diagnosis and image guided surgery", J. Comput. Inf. Tech. 1998, 6(2), 165.

S. Rudin, D.R. Bednarik, C.-Y. Yang: "Real-time equalization of region-of-interest fluoroscopic images using binary masks", Medical Physics 26:(7), 1359-1364, 1999.

N. Robert, P. T. Komljenovic, J.A. Rowlands: "A filtering method for signal equalization in region-of-interest fluoroscopy", Medical Physics 29: (5), 736-747, 2002.

S. Young, V. Pekar, J. Weese: "Vessel segmentation for visualization of MRA with bloodpool contrast agent", Medical Image Computing and Computer Assisted Interventions (MICCAI2001), W.J. Niessen, M.A. Viergever, eds.; Lecture Notes in Computer Science 2208, 2001.

P.J. Keall et al: "Motion Adaptive X-Ray Therapy: A Feasibility Study", Physics in Medicine and Biology, vol. 46, No. 1, pp. 1-10, 2001, 655471.

* cited by examiner

X-RAY UNIT HAVING AN AUTOMATICALLY ADJUSTABLE COLLIMATOR

The invention relates to an X-ray unit for generating images of a body, which unit has an automatically adjustable collimator. Furthermore, it relates to a method for producing X-ray pictures of a body using automatic adjustment of a collimator.

X-ray units for recording medical X-ray images comprise, as a rule, a collimator having nontransparent closure parts and semitransparent diaphragm wedges whose adjustment makes it possible to shape the X-ray beam in such a way that only parts of the patient's body that are of interest are irradiated with the desired radiation intensity. Furthermore, collimators typically comprise filter elements in order to vary the spectrum of the beam in the desired way. The most important advantages of the use of a collimator are in the improvement of the image quality, in the reduction of the risk of radiation damage to a patient (for example, skin damage) and in the reduction of scattered radiation to which the staff are exposed during the image recording. In this connection, the reduction in radiation exposure is important, particularly in view of the prolonged diagnostic and therapeutic interventions accompanied by X-ray fluoroscope observation that are increasingly taking place.

Collimators are at present predominantly adjusted by hand by the attendant staff. However, this is not only relatively cumbersome, but also distracts from the actual activity. The adjustment of the collimators is therefore frequently not carried out, with corresponding disadvantages in regard to image quality and radiation exposure.

U.S. Pat. No. 6,055,259 proposes an automatic adjustment of a collimator to protect the X-ray detector from unattenuated direct radiation. In this case, exploratory X-ray pictures are produced at the beginning of an intervention in which directly irradiated detector zones are automatically distinguished from those that are shaded by the patient's body. The collimator is then adjusted so that the zones not shaded by the body are blocked out in the subsequent X-ray pictures. The method is intended, in particular, for pictures of a patient's legs since, in this case, the parts of the body imaged are relatively narrow and large zones of the detector are exposed to direct radiation. In the case of other medical applications, such as, for example, cardiac interventions, such a method is, however, not of use since the X-ray pictures do not in that case include any zones of direct radiation anyway.

Against this background, it is an object of the present invention to provide means for the simplified utilization of the adjustment possibilities of the collimator of an X-ray unit.

This object is achieved by an X-ray unit having the features of claim 1 and also by a method having the features of claim 10. The subclaims contain advantageous configurations.

The X-ray unit according to the invention serves to generate images of a (biological) body and comprises the following components:

a) An X-ray source for producing an X-ray beam.

b) An automatically adjustable collimator comprising diaphragm elements that are not transparent and/or are semitransparent to X-ray radiation, with which an X-ray beam leaving the X-ray source can be limited in its shape and/or locally attenuated, and/or having filter elements with which the spectrum of the X-ray beam can be varied.

c) An X-ray detector that is disposed in the path of the X-ray beam and the amount of X-ray radiation striking it can be measured with positional resolution, in which connection the body to be imaged is to be disposed between the X-ray source and the X-ray detector.

d) A data processing unit that is coupled to the collimator and the X-ray detector and that is designed to perform the two steps below:

Localization on one or more X-ray pictures of the body to be transmitted by the X-ray detector a region of interest within the body to be X-rayed. These X-ray pictures are also described below for the purpose of differentiation as "first X-ray pictures" without a restriction in regard to the instant of their production being associated therewith. The region of interest (ROI) is, as a rule, predetermined by the particular underlying application. In particular, it can be defined by an organ or a portion of an organ, for example, by a part of a coronary vessel in the case of cardiac interventions. Said region can be localized on an X-ray picture semi-automatically or even fully automatically with the aid of known methods of image analysis, a user in the first case providing interactively certain additional information items, such as, for instance, the beginning and the end of a vessel portion of interest.

Adjustment of the collimator in such a way that the "subsequent" X-ray pictures generated are concentrated on the region of interest. The precise manner of "concentration" of an X-ray picture on a region of interest may take place in various ways depending on the application or depending on the specification of a user. As a rule, the concentration will include a best possible display of the region of interest and a blocking-out of all the body regions not belonging to the region of interest. In this connection, the transition between these two extremes is typically rendered smooth with the aid of wedge-shaped, semi-transparent diaphragm elements so that certain residual information remains detectable in this zone with reduced radiation exposure.

The X-ray unit described has the advantage that it includes a fully automatic and at least largely automated adaptation of a collimator to the display of a region of interest, said region being defined and specified on the basis of the application and the patient. That is to say, that, for example, an intervention at the aorta is based on a region of interest that is different in size and shape from that of interventions at the coronary vessels. It is furthermore of importance that the region of interest is a specific body region, for example an organ or a part of an organ of the body. The imaging method is therefore advantageously oriented towards the anatomy of a patient and not, for instance, towards certain instruments or the like.

In accordance with a preferred configuration of the invention, the region of interest is defined in such a way that all the positions of a body structure to be observed, such as, for example, an organ, that said body structure can assume during a periodic movement of the body are covered in the resultant irradiation field after adjusting the collimator. In many application cases, the position of an organ of interest periodically varies in fact as a result of body movements, such as the heartbeat and/or respiration. In order, nevertheless, to ensure a sufficiently good coverage of the body structure on the X-ray pictures and, on the other hand, to avoid constantly readjusting the collimator, the region of interest is therefore chosen large enough at the outset for all the positions of the organ encountered to be in the imaging region.

Proceeding from a certain body structure to be observed, such as, for instance, an organ, a region of interest of the above-described type can be specified, for example, in that it covers the body structure together with a circumferential peripheral zone of predetermined width. Preferably, the data processing unit is, however, designed to determine a correspondingly widely defined region of interest on the basis of a plurality of first X-ray pictures that originate from various phases of the periodic movement. That is to say the position of a body structure to be observed is always localized in the plurality of X-ray pictures and the region of interest is specified in such a way that a collimator adjusted thereto covers by means of its irradiation field all the positions determined and possibly also an additional (smaller) safety border around it.

As already explained, the region of interest may be a portion of a vessel. In this case, the first X-ray pictures are preferably made in such a way that they display a previously injected contrast medium inside the portion of interest in the vessel system. Furthermore, the data processing unit is at the same time designed to determine the vessel pattern in said portion in the first X-ray pictures from the detection of the contrast medium. In particular, the data processing unit can extract in this regard the variation with time of the front of a contrast-medium injection (bolus) from a plurality of X-ray pictures and use it to determine the vessel pattern.

In accordance with another embodiment, the X-ray unit comprises means for the qualitative and quantitative coverage of a movement of the region of interest in the body, in which connection said movement may be produced, for example, by moving the patient on the examination table or by displacing the examination table. In this connection, the movement should be defined relative to the imaging parts of the X-ray unit so that, for example, a variation in the position of the X-ray source and/or X-ray detector is also detected as a movement of the region of interest. Furthermore, in this configuration of the X-ray unit, the data processing unit is designed to readjust the adjustment of the collimator in such a way that the imaging remains concentrated on the region of interest, that is to say the movement of the region of interest is compensated for in the X-ray pictures produced. This ensures that, despite any movements, the examination region of interest is always imaged, with minimum radiation exposure.

The means of detecting the movement may comprise, in particular, sensors that detect a displacement of the examination table on which the patient is lying. Furthermore, they may comprise sensors for logging the X-ray picture parameters (position, angle, spacings, mode, etc., of the radiation source and of the X-ray detector).

In a preferred embodiment of the above-described X-ray unit, the data processing unit is designed to estimate the movement of the region of interest from an image analysis of the "subsequent" X-ray pictures. That is to say X-ray pictures produced during an examination are constantly examined for whether a movement has taken place in the region of interest. Once such a movement has been detected and its extent has been determined, the data processing unit can respond thereto by means of an appropriate readjustment of the collimator and the region of interest can continue to be kept in the imaging region. Preferably, this procedure is combined with the abovementioned means that determine the variation of boundary conditions (patient table, X-ray unit, etc.) by means of sensors.

The localization of a region of interest on the first X-ray pictures and/or the evaluation of the subsequent X-ray pictures (for instance, for the purpose of movement estimation) will in practice always lead to results subject to uncertainties. For example, an inadequate image quality may make a precise localization of an organ of interest impossible. For this reason, the data processing unit is preferably designed in such a way that it moves the collimator to a specified standard position if the region of interest cannot be localized with adequate certainty from the start or can no longer be adequately localized in the course of the method. In this respect, a quantitative standard of certainty to be applied must be defined by known methods and its maintenance must be checked. The standard adjustment of the collimator is specified in accordance with the requirements of a user for the application case concerned. In particular, the collimator may be opened to a maximum in order to ensure the coverage of the region of interest in the X-ray pictures at all events.

In accordance with another embodiment of the invention, the X-ray unit is designed to undertake a three-dimensional localization of the (three-dimensional) region of interest from the first X-ray pictures. For this purpose, the X-ray unit is typically designed as a rotational X-ray device that generates pictures of the body from various projection directions from which the field of observation, including the region of interest, can be reconstructed three-dimensionally. In this respect, the data processing unit is furthermore designed to readjust the collimator in the event of an alteration in the picture direction during the subsequent (two-dimensional) X-ray pictures in such a way that a concentration continues to exist on the region of interest. With the aid of the three-dimensional localization of the region of interest, it is therefore, for example, also possible to compensate for tilting of the X-ray device.

The invention furthermore relates to a method for generating X-ray pictures of a body that comprises the following steps:

a) generation of at least one first X-ray picture of the body;
b) localization of a region of interest inside the body on the first X-ray picture(s);
c) automatic adjustment of a collimator in such a way that the subsequent X-ray pictures are concentrated on the region of interest.

In general form, the method comprises the steps that can be executed with an X-ray device of the above-described type. Reference is therefore made to the above description of the X-ray unit in regard to the details, advantages and embodiments of the method.

These and other aspects of the invention are apparent from and will be elucidated with reference to the embodiments described hereinafter.

FIG. 1 shows diagrammatically the components of an X-ray unit according to the invention.

In order to generate an X-ray picture of a body of a patient 5, the X-ray unit comprises an X-ray radiation source 7 having an X-ray tube that generates X-ray radiation with the aid of an X-ray voltage provided by a generator, and also an X-ray detector 4 that measures with positional resolution the X-ray radiation transmitted by the body of the patient 5. The X-ray detector 4 is furthermore coupled to a picture acquisition unit 1 for reading out the individual image sensors. The control of the X-ray unit and the processing of the acquired (digitized) X-ray images are effected by a data processing unit 2 that, for this purpose, is coupled to the picture acquisition 1 unit and the X-ray radiation source 7. Furthermore, the data processing unit 2 is coupled to a system console 8 via which a user can input commands and can control the recording procedure and also to a display unit 3 for displaying the X-ray picture taken.

The X-ray unit furthermore comprises a collimator 6 of which the FIGURE indicates two closure parts intervening in the X-ray beam and a filter as representative. The collimator furthermore includes a so-called primary-beam filter (not shown) comprising an iris that transmits only a conical radiation beam of the radiation generated by the X-ray tube, and also a beam filter. Beam filters in the collimator are frequently used to control the radiation quality and to reduce the patient dose.

The collimator 6 is likewise coupled to the data processing unit 2, the latter being able to transmit commands for adjusting the filter elements and diaphragm elements on the collimator 6 to the desired positions, where said commands are executed by a suitable automatic positioning system.

In the FIGURE, the boundaries of the X-ray cone that result from a maximum opening of the collimator 6 are indicated by broken lines. For most examinations, however, only a very much smaller region of the body, for example, the diagrammatically indicated portion of a vessel 10, is of interest. In order to minimize the radiation exposure of patient and personnel and to improve the image quality, the X-ray beam is therefore advantageously limited by the collimator 6 in such a way that it essentially covers only the region of the body of interest. The application-specific method explained below is intended to relieve the physician in this respect of a manual adjustment of the collimator 6 in that the variously shaped diaphragm and filter units of the collimator 6 are automatically adjusted to suit the anatomy of the patient 5.

In this connection, in a first step, an organ 10 of interest or a part thereof is fully automatically or semi-automatically segmented in the data processing unit 2 on "first" X-ray pictures generated by the X-ray unit. Using the result of this segmentation, an application-specific "region of interest", referred to below as ROI, is then specified. The data processing unit 2 then drives the collimator 6 in such a way that the diaphragm and filter elements are adjusted in accordance with a restriction of the X-ray beam to the specified ROI (reference numeral 9 on the image shown by the monitor 3).

In particular, in the case of cardiac interventions, the specification of an ROI can comprise the estimate of movement during a heart cycle and/or a respiratory cycle to ensure that the organ (part) 10 of interest always remains in the image despite spontaneous movement. Furthermore, movement can be continuously detected and estimated after the initial adjustment of the collimator 6 so that the collimator 6 can be readjusted accordingly in the event of a movement (going beyond heartbeat/or respiration). Should it not be possible to adjust the collimator 6, for example because the projection direction of the X-ray unit has been changed, the collimator 6 is preferably opened up to a standard adjustment in order to ensure coverage of the ROI.

The method sketched generally above is now explained in greater detail using the example of the treatment of an aortic aneurysm. In such a treatment, a stent attached to a catheter is introduced into the vessel system up to the point of the aneurysm. The stent is then released, whereupon it unfolds and strengthens the aorta by generating a new, more stable channel for the blood flow, while the aneurysm is isolated from the circulation. Typical features of such an intervention are:

1. a clear definition of the region of interest ROI by the shape of the aorta;
2. as a rule, very little patient movement;
3. a movement of the examination table that takes place as a rule only along the axis of the aorta;
4. imaging of the lesion in the anterior-posterior direction, during which the projection angle is normally not changed during the intervention.

In the first step in the method, the aorta and associated vessel portions are segmented from an angiographic picture sequence that is typically acquired at the start of the intervention. In this connection, by means of an analysis of certain picture properties (for example checking whether a subtractive image is involved and whether the sequence shows a bolus of contrast agent that is flowing through the vessel system), it can be decided whether a sequence is suitable for an automatic segmentation of the ROI. Alternatively, the system can be designed in such a way that the physician activates the "ROI imaging" protocol precisely when the last sequence chose precisely the clinically relevant region.

After this general classification step, a single image is determined from the available angiographic sequence, which image serves as a master for the subsequent segmentation step. Either an image is selected by image analysis methods or the minimum image is calculated from all the images of the angiographic sequence or a selection of them. The clinically relevant ROI can then be segmented automatically with the aid of said individual image. In this connection, an anatomical model may be helpful in distinguishing between the aorta and relevant vessels, on the one hand, and smaller vessels, on the other.

A region of interest ROI is defined, for example, by a contour that includes the segmentation result. The diaphragm and filter elements in the collimator 6 can then be adjusted in such a way that the region of interest is now imaged. The definition of the region of interest ROI and the collimator adjustment can be executed completely automatically by detecting the inflow of the contrast agent.

During the subsequent intervention, an image of the initially recorded angiographic sequence comprising the corresponding region of interest is normally registered by means of a current image. Typically, the imaging is performed during the intervention in a low-dose fluoroscopic mode (LDF) and generally without administering a contrast agent. Apart from the instruments opaque to X-rays that may be present, only certain background information (for example, vertebral bodies, tissue) are visual on the current pictures. In the prior art, however, various registration methods and similarity measures are known with which registration is rapidly and reliably possible on the basis of differences in the images (cf. T. M. Buzug, J. Weese: "Image registration for DSA quality enhancement", Comput. Med. Imag. Graph. 1998, 22, 103; T. M. Buzug, J. Weese: "Voxel-based similarity measures for medical image registration in radiological diagnosis and image guided surgery", J. Comput. Inf. Tech. 1998, 6(2), 165).

Furthermore, a movement detection and estimation has to be performed in order to adjust the collimator 6 in the event of occurrence of a movement (table tilting, patient movement, etc.). In this operation, information items and parameters of the imaging system, such as, for example, the projection direction, the position of the examination table and the II mode, can be used to obtain a more reliable result. If the movement should be so large that the specified ROI cannot be localized in the current image, the diaphragm and filter elements of the collimator are removed from the field of view in order to ensure imaging and to make the method as robust, automated and reliable as possible.

Furthermore, image homogenization procedures can be used for an optimum quality in order to correct brightness differences between the attenuated image regions and the unattenuated image regions (S. Rudin, D. R. Bednarik, C.-Y. Yang: "Real-time equalization of region-of-interest fluoroscopic images using binary masks", Medical Physics 26:(7), 1359-1364, 1999; N. Robert, P. T. Komljenovic, J. A. Rowlands: "A filtering method for signal equalization in region-of-interest fluoroscopy", Medical Physics 29: (5), 736-747, 2002). Noise filtering can be performed to reduce noise in image areas covered by diaphragms/filters.

The steps in the method explained above in greater detail can be modified in a suitable way for other applications, in which connection the choice between various procedures implemented in the software of the data processing unit 2 can be made by the user at the start of an intervention. For example, in the treatment of a stenosis in the coronary arteries (PTCA: percutaneous transluminal coronary angioplasty), it may be impossible to identify the segment of a coronary vessel of interest fully automatically. In an interactive intermediate step, a cardiologist may therefore display a starting point and a finishing point of the vessel segment of interest on an angiographic image. An automatic segmentation of the vessel segment may then take place, for example, using a method based on a front propagation and a vessel filter (S. Young, V. Pekar, J. Weese: "Vessel segmentation for visualization of MRA with bloodpool contrast agent", Medical Image Computing and Computer Assisted Interventions (MICCAI2001), W. J. Niessen, M. A. Viergever, eds.; Lecture Notes in Computer Science 2208, 2001).

Furthermore, in such an application, it is undesirable to adjust the filter elements of the collimator 6 constantly as a function of heartbeat and respiration. For this reason, the region of interest is defined large enough for the associated collimator adjustment to cover the vessel segment of interest during all the heartbeat and respiration phases that occur. Similarly, account must also be taken of heartbeat and respiration during movement estimation and compensation for the purpose of adapting the collimator adjustment.

If data are available from a three-dimensional X-ray angiography, the organ of interest is preferably defined and segmented three-dimensionally. With the aid of such three-dimensional data, the collimator 6 can then also be readjusted if the projection direction is changed during the subsequent X-ray pictures.

Extensive automation of the system described ensures that the advantages of imaging limitation to a region of interest can also be used in practice. The radiation exposure can thereby be minimized for patients and staff. The image quality in the region of interest increases as a result of less scattered radiation in the periphery. Therefore, either the visibility of spirals or wire meshes for embolizing vessels, stents and the like can be improved or the dose can be reduced with constant visibility of details. Since not only the forward scattering but also the back scattering is reduced, the radiation exposure is reduced for the medical staff.

The invention claimed is:

1. An X-ray unit for generating imagings of a body, comprising:
   a) an X-ray source (7);
   b) an automatically adjustable collimator (6) including diaphragm and filter elements for limiting, locally attenuating and/or filtering an X-ray beam output from the X-ray source;
   c) an X-ray detector (4) for detecting X-rays; and
   d) a data processing unit (2) coupled to the collimator (6) and to the X-ray detector (4), wherein the data processing unit is designed to localize a region of interest (9) inside the body on at least a first X-ray picture of the body transmitted by the X-ray detector (4) and to transmit commands to the collimator to adjust the diaphragm and filter elements of the collimator (6) in accordance with a restriction of subsequent X-ray beams to the localized region of interest such that the subsequent X-ray beams and corresponding detected X-rays result in subsequent X-ray pictures that are concentrated on the localized region (9) of interest, wherein a concentration of the subsequent X-ray pictures includes (i) a best possible display of the localized region of interest and (ii) a blocking-out of all body regions not belonging to the localized region of interest, further including a smooth transition zone between the display of the localized region of interest and the blocking-out so that certain residual information remains detectable in the transition zone with reduced radiation exposure.

2. An X-ray unit as claimed in claim 1, wherein an irradiation field of the collimator (6) adjusted on the localized region (9) of interest is defined by an organ or part (10) of an organ.

3. An X-ray unit as claimed in claim 1, wherein the region of interest (9) covers possible positions of a body structure (10) during a periodic movement of the body structure.

4. An X-ray unit as claimed in claim 3, wherein the data processing unit (2) is further designed to determine the region of interest (9) on the basis of a plurality of first X-ray pictures from different phases of the periodic movement of the body structure.

5. An X-ray unit as claimed in claim 1, wherein the at least a first X-ray picture comprises first X-ray pictures that display a contrast agent inside a vessel system of vessels and wherein the data processing unit (2) is further designed to determine a course of the vessels from detection of the contrast agent on the first X-ray pictures.

6. An X-ray unit as claimed in claim 1, wherein the data processing unit is further designed to detect a movement of the localized region of interest (9) of the body, and to readjust the adjustment of the collimator (6) in response to detection of movement of the localized region of interest such that the concentration on the region of interest (9) remains intact.

7. An X-ray unit as claimed in claim 6, wherein the data processing unit (2) is still further designed to estimate the movement of the localized region (9) of interest from an image analysis of the subsequent X-ray pictures.

8. An X-ray unit as claimed in claim 1, wherein the data processing unit (2) is designed to move diaphragm and filter elements of the collimator (6) to a specified standard adjustment if the region (9) of interest cannot be localized or cannot be localized any longer with adequate certainty.

9. An X-ray unit as claimed in claim 1, wherein the data Processing unit is further designed to undertake a three-dimensional localization of the region of interest from the first X-ray pictures, and in that the data processing unit (2) is furthermore designed to readjust the diaphragm and filter elements of the collimator (6) in the event of an alteration in a recording direction while the subsequent X-ray pictures are being taken.

10. A method of generating X-ray pictures of a body, comprising:
   a) generating at least a first X-ray picture of the body;
   b) localizing a region (9) of interest inside the body on the first X-ray picture; and
   c) performing an automatic adjustment of diaphragm and filter elements of a collimator (6) in accordance with a restriction of subsequent X-ray beams to the localized region of interest such that subsequent generated X-ray pictures are concentrated on the localized region (9) of interest, wherein a concentration of the subsequent X-ray pictures includes (i) a best possible display of the localized region of interest and (ii) a blocking-out of all body regions not belonging to the localized region of interest, further including a smooth transition zone between the display of the localized region of interest and the blocking-out so that certain residual information remains detectable in the transition zone with reduced radiation exposure.

* * * * *